(12) United States Patent
Liu

(10) Patent No.: US 8,922,365 B2
(45) Date of Patent: Dec. 30, 2014

(54) METHODS AND SYSTEMS FOR MONITORING AND ALERTING BODY TEMPERATURE

(71) Applicant: Weidong Liu, Chongqing (CN)

(72) Inventor: Weidong Liu, Chongqing (CN)

( * ) Notice: Subject to any disclaimer, the term of this patent is extended or adjusted under 35 U.S.C. 154(b) by 69 days.

(21) Appl. No.: 13/660,736

(22) Filed: Oct. 25, 2012

(65) Prior Publication Data

US 2013/0181831 A1   Jul. 18, 2013

(30) Foreign Application Priority Data

Jan. 18, 2012  (CN) .......................... 2012 1 0014431

(51) Int. Cl.
  *G08B 1/08*  (2006.01)
(52) U.S. Cl.
  USPC ............... 340/539.12; 340/539.11; 340/571; 340/669; 340/573.1; 600/22; 600/300; 600/549; 600/412; 600/301; 128/898
(58) Field of Classification Search
  CPC .. A61B 2503/04; A61B 2503/08; A61B 5/01; A61B 5/6804; A61B 5/746; G01K 13/002; G01K 1/02
  USPC ............... 340/539.12, 539.11, 571.31, 669, 340/573.1; 600/301, 549, 300, 22, 359, 600/412; 374/111; 128/898
  See application file for complete search history.

(56) References Cited

U.S. PATENT DOCUMENTS

| | | | |
|---|---|---|---|
| 6,238,354 B1 * | 5/2001 | Alvarez ....................... | 600/549 |
| 6,527,711 B1 * | 3/2003 | Stivoric et al. ............... | 600/300 |
| 6,547,745 B1 * | 4/2003 | Rubinstein ................... | 600/549 |
| 6,641,544 B2 * | 11/2003 | Liu .............................. | 600/549 |
| 6,653,605 B2 * | 11/2003 | Kneuer ........................ | 219/494 |
| 7,625,117 B2 * | 12/2009 | Haslett et al. ................ | 374/111 |
| 7,942,825 B2 * | 5/2011 | Ranganathan et al. ....... | 600/549 |
| 7,991,514 B2 * | 8/2011 | Berenbaum et al. ......... | 700/300 |
| 2004/0116822 A1 * | 6/2004 | Lindsey ........................ | 600/549 |
| 2008/0214949 A1 * | 9/2008 | Stivoric et al. ............... | 600/549 |

* cited by examiner

*Primary Examiner* — Benjamin C Lee
*Assistant Examiner* — Chico A Foxx
(74) *Attorney, Agent, or Firm* — Hamre, Schumann, Mueller & Larson, P.C.

(57) ABSTRACT

Embodiments disclosed herein relate to systems and methods for monitoring and alerting a body temperature of a person under guardianship. A wireless signal emitting body temperature sensor is configured to transmit a wireless signal including a detected temperature value. The wireless signal is received by a wireless signal receiving chip of a wireless signal receiving and processing precaution device carried by a guardian, and processed by a central processing chip. If the detected value is over the maximum value or is under the minimum value, an alarming signal will timely notify the guardian about abnormality in the body temperature of the person under guardianship.

2 Claims, 2 Drawing Sheets

METHODS AND SYSTEMS FOR MONITORING AND ALERTING BODY TEMPERATURE

FIELD OF TECHNOLOGY

Embodiments disclosed herein relate to systems and methods to measure a temperature or heat, particularly systems and methods using a thermo-sensor to monitor and alert cold/hot condition.

TECHNOLOGY BACKGROUND

As widely known, when a change of 3° C. to 4° C. in an ambient temperature, a human body can self-regulate and maintain a stable body temperature. When a change exceeds such a scope, putting on or taking off clothing may be required to maintain a stable body temperature. However, an infant's body temperature regulating center has not fully developed, and may be lack of the ability to regulate her body temperature. If clothing is not timely put on to or taken off from the infant, excessively high or low body temperature is likely to happen resulting the infant's sicknesses. Because of slowing down in metabolism and reduced sensitivities in body temperature regulating center, elder people may not timely sense the temperature change; and because of reduced body-temperature self-regulating ability, they need to put on or take off clothing in a more timely manner to avoid sicknesses caused by excessive heat or cold. Toddlers often slip out of quilts during sleep and expose their abdomens, likely leading to catching cold and resulting abdominal sicknesses. Children during their ordinary sport exercises often produce large amount of body heat, and if their clothing is not taken off timely they may sweat heavily and thus likely catch cold or other illnesses. Therefore, timely control of body surface temperature of infants, elder people, children, etc., and timely adding on or taking off clothing can directly affect their health.

To keep a normal body temperature, adding up or taking off clothing, or changing ambient temperature is required to change body surface temperature. However because infants may not talk, and elder people may not timely sense the change in temperature, their guardians will have to decide whether to add on or take off clothing by detecting a change in the body temperature.

However, accuracy of human sensory is unreliable, and the guardians may not be able to make timely decisions.

Therefore, a body temperature monitoring and alarming system is needed to monitor a change in the body temperature of the person under guardianship, to alert the guardian and to provide information whether adding on or taking off clothing is required to maintain the body temperature of the person under guardianship.

SUMMARY

The technical problem intended to be solved is to provide a body temperature monitoring and alarming system and method, which can detect body surface temperature changes of a person under guardianship, and timely alert a guardian with information for the guardian to decide whether to add on or take off clothing in order to maintain a body surface temperature of the person under guardianship.

In order to achieve the purposes above, some embodiments may include a body temperature monitoring and alarming system, which may include a wireless signal emitting body temperature sensor and a wireless signal receiving and processing precaution device. The wireless signal emitting body temperature sensor may further include a temperature sensor, a signal processing chip, and a wireless signal emitting chip. In some embodiment, the wireless signal emitting body temperature sensor may include the temperature sensor, the signal processing chip and the wireless signal emitting chip connected in series in that order and sealed in a water proof outer shell. The wireless signal receiving and processing precaution device may further include a wireless signal receiving chip, a signal fine-tuning terminal, a central processing chip, a function button, a precaution device, and supporting electronic components. In some embodiments, the wireless signal receiving and processing precaution device may include the wireless signal receiving chip, the signal fine-tuning terminal, the central processing chip, the function button, the precaution device and the supporting electronic components connected in series in that order. The temperature sensor may be configured to detect a temperature value, and the temperature value may be transmitted to the signal processing chip via flexible wires. After the temperature value being processed, a wireless signal may be emitted from the wireless signal emitting chip. The wireless signal may be received by the wireless signal receiving chip, and may be fine-tuned by the signal fine-tuning terminal and processed by the central processing unit, and the precaution device may be signaled. The power supply to the wireless signal receiving and processing device may be configured to be turned on, and the threshold values and any increase or decrease in the threshold values are set up and stored within 3 minutes. After 3 minutes the wireless emitting chip in the wireless signal emitting body temperature sensor is configured to feed in temperature values every 30 seconds, such information may be stored by the central processing chip. After the temperature sensor feeds in temperature values for 8 times, the signal processing chip may process the information by excluding the highest temperature value and the lowest temperature value; calculating the average value of the remaining 6 temperature values to an accuracy of the first decimal place; adding the preset increasing value to the average value and setting the result as the maximum value; and subtracting the preset decrease value from the average value and setting the result as the minimum value. The maximum value and the minimum value are stored and used in the monitoring and cautioning working mode.

In some embodiments, the method may further include sewing the wireless signal emitting body temperature sensor onto clothing or put the sensor into a pocket of the clothing; during a static state a guardian makes sure that a person under guardianship is in a most comfortable and warm condition; turning on a power supply of the wireless signal receiving and processing precaution device. Within 3 minutes after turning on the power supply, the increase value and decrease value based on a physical condition of the person under guardianship are set up: if such a person's physical condition is relatively good, adding 2° C. to the average temperature value and setting the result as the maximum value, and subtracting 2° C. from the average temperature value and setting the result as the minimum value; sound and light feedbacks are provided in each step indicating setting up is successfully made. If such a person has a relatively high body temperature, the maximum value and the minimum value can be changed by using a function button, one push for a 0.5° C. increase; when the increased value reaches 37.5° C., a long push of the function button for 3 seconds or more restores the value to default; sound and light feedbacks are provided in each step indicating setting up is successfully made. After setting up the values the central processing units begins to work, and after a sound notice the monitoring and cautioning working mode begins.

When a change in the ambient temperature or other factors resulting body temperature exceeding the preset values, light and sound notices are provided to alert the guardian in real-time.

Furthermore, in some embodiments in order to more properly detect a temperature in abdomen and back, the wireless signal emitting body temperature sensor is placed within a 20 mm radius from the navel and the "Fei-Yu" acupuncture points. The "Fei-Yu" acupuncture point locates on the back of a human body, under the third spinous process of the thoracic vertebra, within two-finger width to the left and right.

Placing the temperature sensor near the navel and the "Fei-Yu" acupuncture points allows an accurate detection of the temperature near the abdomen area and the lung area, thus prevents illnesses caused by the abnormal temperature in the abdomen and lung areas.

Furthermore, in some embodiments the wireless connection distance between the wireless signal emitting body temperature sensor and the wireless signal receiving and processing precaution device is 50 meters.

When the person under guardianship is away from the guardian, within the 50-meter range the wireless signal receiving and processing precaution device signals and notifies the guardian using different sounds and lights. When the distance between the wireless signal emitting body temperature sensor and the wireless signal receiving and processing precaution device exceeds the 50-meter range, and the distance is not restored to the 50-meter range within 30 seconds, the wireless signal emitting body temperature sensor restores to an alarm mode, and the wireless signal receiving and processing precaution device may be turned off automatically.

Furthermore, the default threshold value for the central processing unit is 36.5° C., and the preset increase value and the preset decrease value are both 1.5° C.

Furthermore, if the result by adding the preset increase value to the average value exceeds the threshold value, using the threshold value as the maximum value, and automatically using a value as the minimum value by subtracting two times of the preset decrease value from the threshold value.

By setting the maximum value and the minimum value, after the central processing chip receives and processes the detected values from the wireless signal emitting body temperature sensor, if the detected value is higher than the maximum value or is lower than the minimum value, the wireless emitting chip signals the guardian carrying a wireless signal receiving and processing precaution device and alerts the abnormality in body temperature of the person under guardianship.

DRAWINGS

The following is a detailed explanation of embodiments herein using drawings.

DETAILED DESCRIPTION

Figure 1:
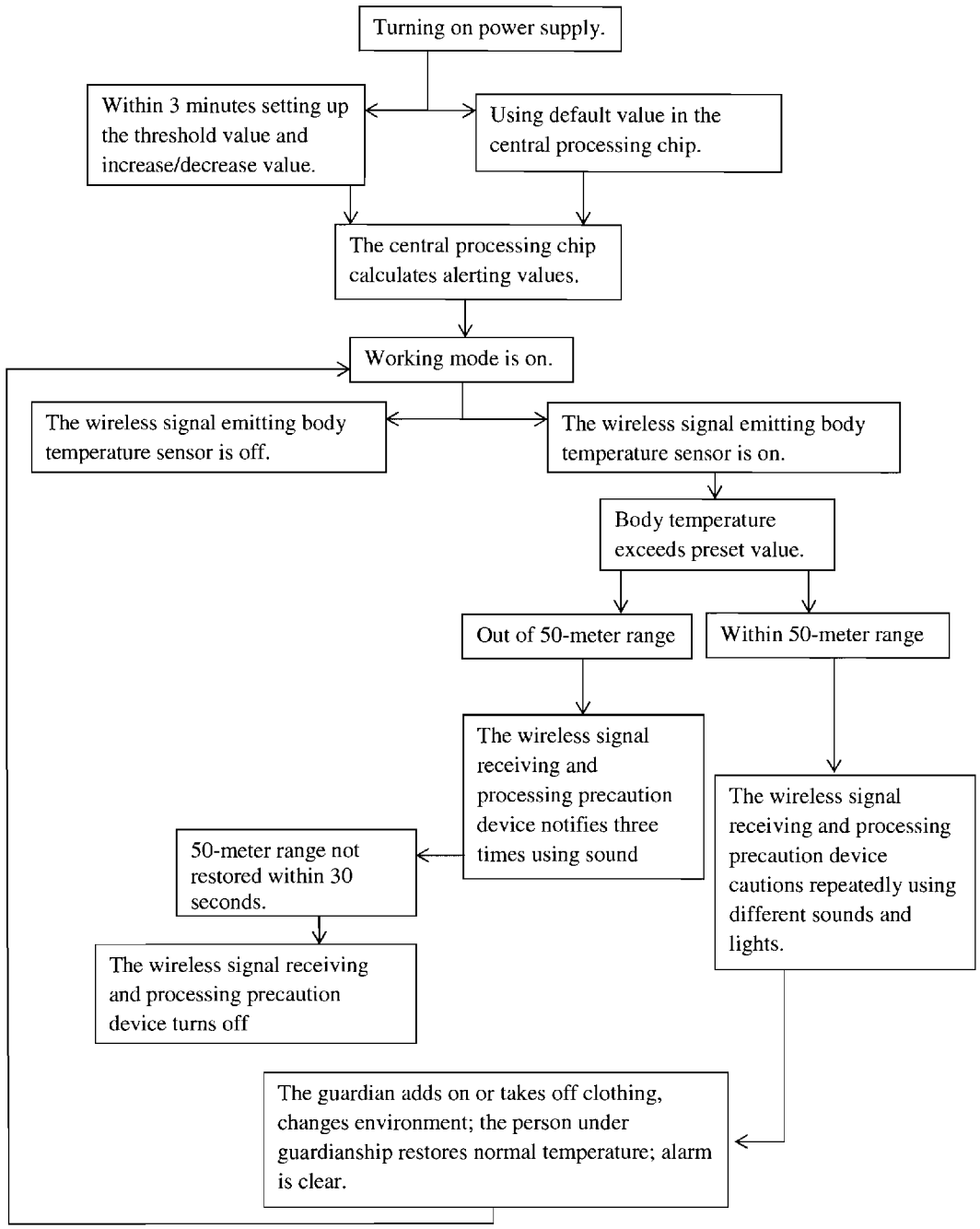
FIG. 1 illustrates an embodiment of a method for using the body temperature monitoring and alarming system to monitor and alarm.
Figure 2:
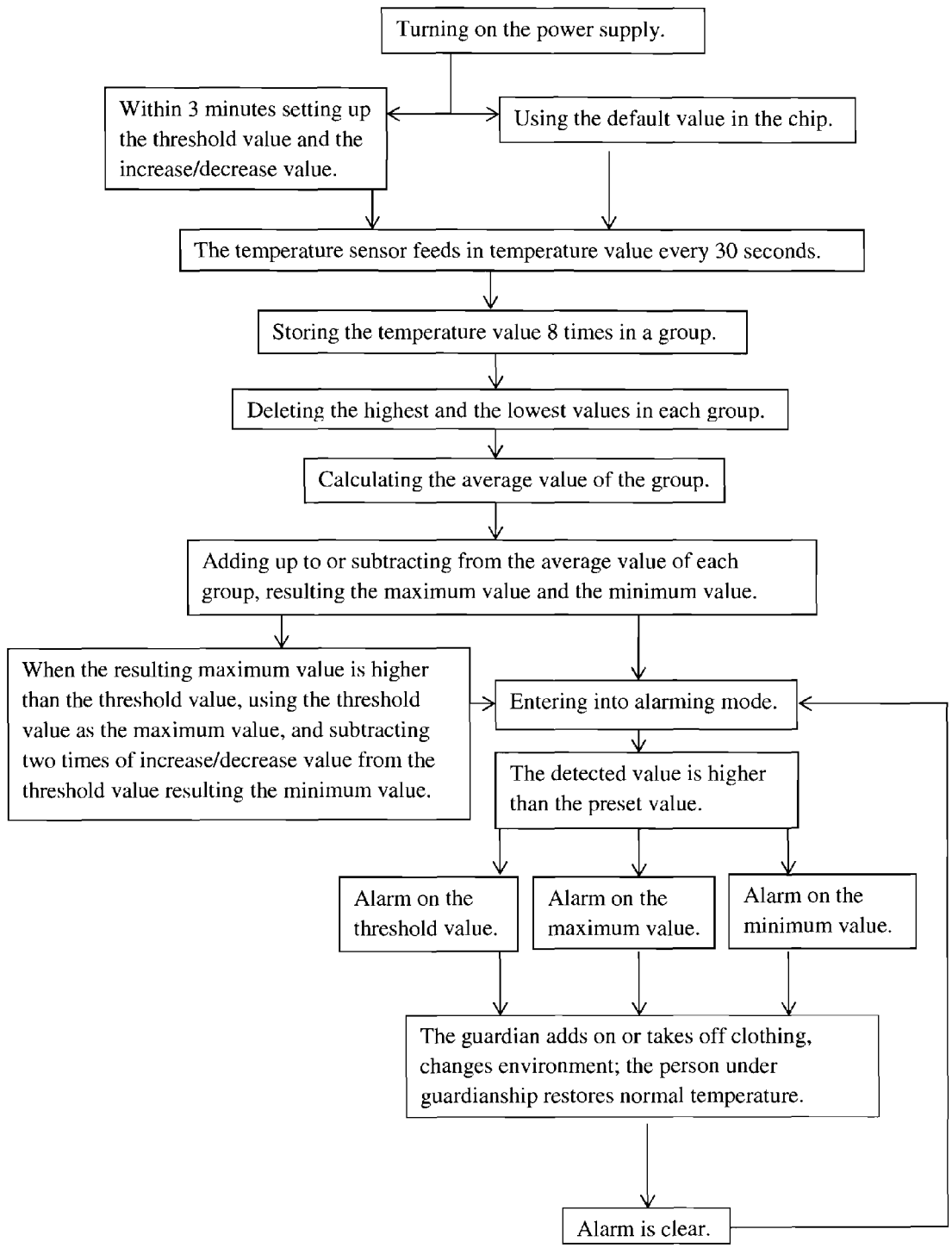
FIG. 2 illustrates an embodiment of a method for processing body temperature information by the central processing chip in FIG. 1.

As shown in FIG. 1 and FIG. 2, a body temperature monitoring and cautioning device system includes a wireless signal emitting body temperature sensor and a wireless signal receiving and processing precaution device. The wireless signal emitting body temperature sensor further includes a temperature sensor detecting a body temperature, a signal processing chip connected to the temperature sensor via a circuit, and a wireless signal emitting chip connected to the central processing chip via a circuit, all of the above units sealed in a water-proof outer shell. A wireless signal is emitted from the wireless signal emitting chip. The wireless signal is received by a wireless signal receiving chip, and is fine-tuned by a signal fine-tuning terminal, and is processed by a central processing chip. The processing in the central processing chip includes comparing a set of preset maximum value, minimum value and threshold value, once the detected value exceeds the preset values, the central processing chip controls the wireless signal receiving and processing precaution device to signal an alarm.

A method for monitoring a body temperature and alerting a guardian include: sewing the wireless signal emitting body temperature sensor onto clothing or put the sensor into a pocket of clothing; during a static state a guardian makes sure that a person under guardianship is in a most comfortable and warm condition, turning on the power supply of the wireless signal receiving and processing precaution device. Within 3 minutes after turning on the power supply the increase value and decrease value based on a physical condition of the person under guardianship are set up: if such a person's physical condition is relatively good, adding 2° C. to the average temperature value and setting the result as the maximum value, and subtracting 2° C. from the average temperature value and setting the result as the minimum value; sound and light feedbacks are provided in each step indicating setting up is successfully made. If such person has a relatively high body temperature, the maximum value and the minimum value can be changed by using the function button, one push for a 0.5° C. increase; when the increased value reaches 37.5° C., a long push of the function button for 3 seconds or more restores the value to the default values; sound and light feedbacks are provided in each step indicating setting up is successfully made. After setting up the values the central processing units begins to process and after a sound notice, the monitoring and cautioning working mode begins. When a change in the ambient temperature or other factors resulting body temperature exceeding the preset values, light and sound notices are provided to caution the guardian in real-time.

The power supply to the wireless cautioning signal receiving processing device is turned on, and the threshold values and any increase or decrease in value are set up and stored within 3 minutes. After 3 minutes the wireless emitting chip in the wireless signal emitting body temperature sensor feeds in temperature values every 30 seconds, such temperature values will be stored by the central processing chip. After the temperature sensor feeds in temperature values for 8 times, the signal processing chip processes the temperature values by excluding the highest temperature value and the lowest temperature value; calculating an average value of the remaining 6 temperature values to an accuracy of the first decimal place; adding the preset increasing value to the average value and setting the result here as the maximum value; and subtracting the preset decrease value from the average value and setting the result here as the minimum value. The maximum value and the minimum value are stored and the monitoring and cautioning working mode begins.

The above is merely a preferred embodiment of this application, and it is understood that a person skilled in this art can make alternations and improvements within the scope of this application so long as they do not differ from the principles of the embodiments as disclosed herein. Such alternations and improvements shall not affect the practicability and utility of the embodiments as disclosed herein.

The invention claimed is:

1. A method for monitoring body temperature and alarming a guardian comprising:
   detecting a temperature value and transmitting the temperature value to a wireless signal receiving and processing precaution device comprising a wireless signal receiving chip, a fine-tuning terminal, and a central processing chip; said detecting and transmitting comprising:
      detecting body temperature to generate a temperature value by a temperature sensor;
      transmitting the temperature value to a signal processing chip via flexible wires;
      processing the temperature value by the signal processing chip;
      emitting from a wireless signal emitting chip, a wireless signal of the processed temperature value;
   receiving the wireless signal by the wireless signal receiving chip;
   fine-tuning the received wireless signal by the signal fine-tuning terminal;
   processing the fine-tuned wireless signal by the central processing chip to generate processed signals; and
   sending the processed signals to a precaution device for alarming the guardian;
   wherein receiving and processing the temperature value signal by the wireless signal receiving and processing precaution device comprising:
      turning on a power supply of the wireless signal receiving and processing precaution device;
      setting up and storing a threshold value and any preset increase or decrease in the threshold value within 3 minutes;
      after 3 minutes, feeding in temperature values every 30 seconds from the temperature sensor;
      storing the temperature values in the central processing chip;
      after said feeding in the temperature values for 8 times, processing such fed temperature values by the central processing chip, comprising:
      excluding the highest temperature value and the lowest temperature value;
      calculating an average value of the remaining 6 temperature values to an accuracy of one decimal place;
      adding a preset increasing value to the average value and setting the result as a maximum value, such that if a result by adding the preset increase value to the average value exceeds the threshold value, using the threshold value as the maximum value, and automatically using a value as a minimum value by subtracting two times of the preset decrease value from the threshold value; otherwise subtracting the preset decrease value from the average value and setting the result here as the minimum value, and using the threshold value as the maximum value;
      storing the maximum value and the minimum value; and
      monitoring body temperature to alarm the guardian based on the detected temperature values against the stored maximum and minimum values.

2. The method for monitoring body temperature and alarming a guardian of claim 1, wherein a default threshold value for the central processing unit is 36.5° C., and a preset increase value and the preset decrease value are both 1.5° C.

* * * * *